(12) United States Patent
Evert

(10) Patent No.: US 6,291,632 B1
(45) Date of Patent: Sep. 18, 2001

(54) MICROSPHERES OF MELAMINE

(75) Inventor: Scott Evert, Tipp City, OH (US)

(73) Assignee: Grantec Inc., Dayton, OH (US)

( * ) Notice: Subject to any disclaimer, the term of this patent is extended or adjusted under 35 U.S.C. 154(b) by 0 days.

(21) Appl. No.: 09/597,323

(22) Filed: Jun. 19, 2000

Related U.S. Application Data

(63) Continuation-in-part of application No. 09/208,927, filed on Dec. 10, 1998, now abandoned.

(51) Int. Cl.[7] .................................................. C08G 12/30
(52) U.S. Cl. ........................................... 528/254; 528/230
(58) Field of Search ..................................... 528/254, 236

(56) References Cited

U.S. PATENT DOCUMENTS

| | | | |
|---|---|---|---|
| 3,904,575 | * 9/1975 | Satokawa et al. | 523/221 |
| 5,614,313 | * 3/1997 | Mills et al. | 428/327 |
| 5,827,615 | * 10/1998 | Touhsaent et al. | 428/463 |
| 5,830,548 | * 11/1998 | Anderson et al. | 428/36.4 |

* cited by examiner

*Primary Examiner*—Duc Truong
(74) *Attorney, Agent, or Firm*—Patrick J. Walsh

(57) ABSTRACT

Microspheres of polymerized melamine formaldehyde resin in spherical form with the microspheres having particle size in a range of 5–15 microns, with the microshperes exhibiting a low coefficient of friction, and providing silky smoothness and opacity when added to other formulations such as cosmetics.

8 Claims, 1 Drawing Sheet

MICROSPHERES OF MELAMINE

This application in a continuation-in-part of application Ser. No. 09/208,927 filed Dec. 10, 1998, now abandoned.

BACKGROUND OF THE INVENTION

The present invention relates to compositions having lubricity, smoothness, and opacity as distinguishing characteristics. In one aspect the invention relates to cosmetic formulations with specific reference to an additive to a formulation for achieving a silky smooth feel, and opacity in filling or smoothing skin surfaces.

SUMMARY OF THE INVENTION

The present invention is directed to microspheres of a polymer which exhibits superior properties as a lubricant per se and for improving the lubricity of other products. Microspheres of the polymer also have use for coating applications in other products, and in cosmetics for imparting a silky feel to skin lotions where a filling or smoothing of the skin is desired.

The invention comprises microspheres of polymerized melamine formaldehyde resin. The unique feature resides in the polymer being formed into microscopic spheres which are perfectly spherical. The microscopic spheres function as round ball bearings, and greatly reduce friction and drag. The microscopic spheres may be incorporated as a lubricant in other compositions to greatly reduce the friction of the composition.

Microspheres of polymerized melamine formaldehyde resin have a coefficient of friction substantially less than spherical silica, titanium dioxide, talc, porous spherical nylon, and boron nitride using a standard test method.

OBJECTS OF THE INVENTION

An object of the invention is to provide microspheres of a melamine polymer for use as a lubricant.

An object of the invention is to provide microspheres of a melamine polymer as providing opacity to compositions.

Another object of the invention is to provide a lubricant for greatly reducing the friction and drag of other compositions.

Another object of the invention is to provide microspheres of a melamine formaldehyde polymer having a coefficient of friction substantially lower than that of other known solid lubricants.

Other and further objects of the invention will become apparent with an understanding of the following detailed description of the invention or upon employment of the invention in practice.

A preferred embodiment of the invention has been chosen for detailed description to enable those having ordinary skill in the art to which the invention appertains to readily understand how to construct and use the invention and is shown in the accompanying drawing in which.

DETAILED DESCRIPTION OF THE PREFERRED EMBODIMENT

Figure 1:
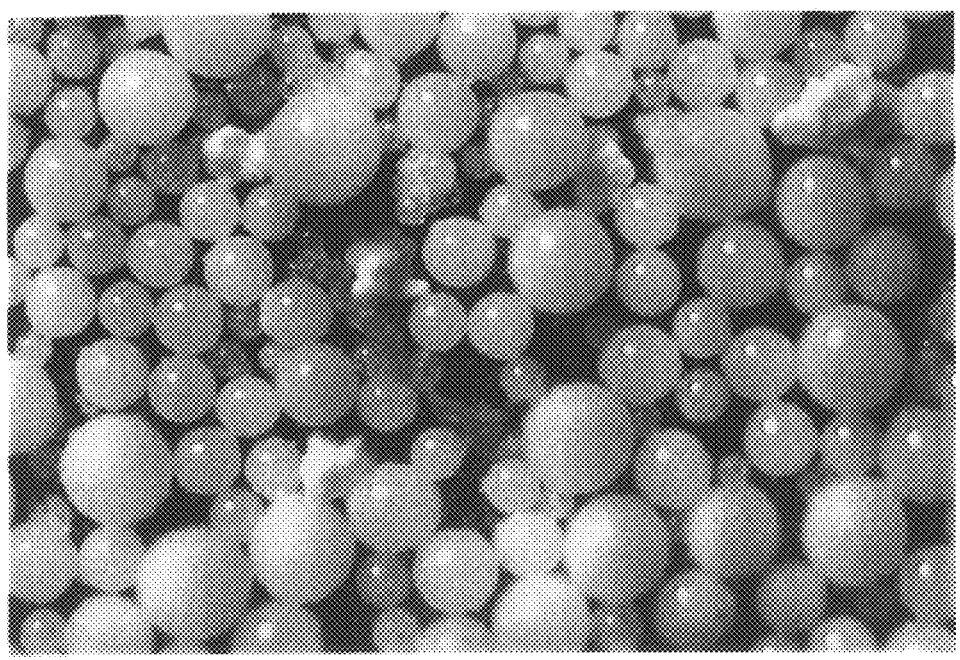
FIG. 1 is a light microscopic photograph of microspheres of melamine formaldehyde polymer at 500× magnification.

Referring to the drawing, FIG. 1 is a microscope photograph of microspheres of polymerized melamine formaldehyde resin comprising the present invention. The microspheres are perfectly spherical and have an average particle size of 5–15 microns. The microspheres are in the form of round ball bearings, that when added to another composition greatly reduce the coefficient of friction of the composition. Preferably, the microspheres have a moisture content less than 2 percent by weight.

The microspheres provide superior opacity with an ultra smooth feel, thereby performing well in cosmetic formulations where a smoothing or filling of the skin surface is desired.

Figure 2:
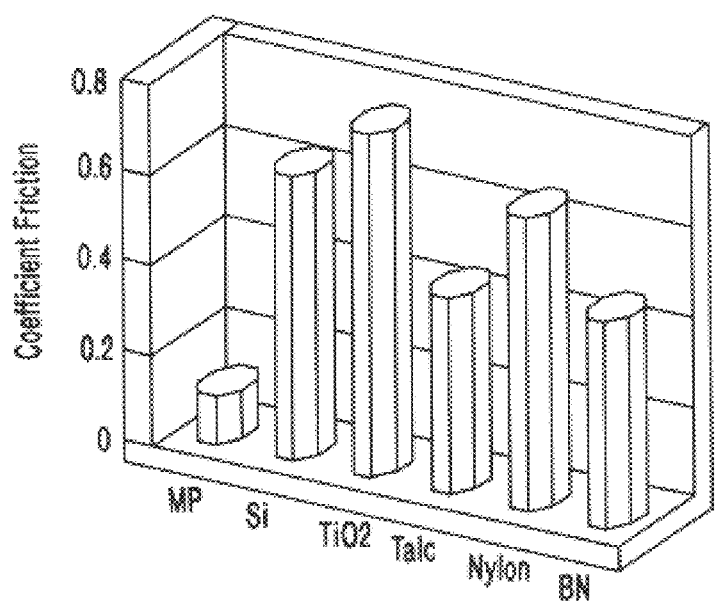
FIG. 2 is a bar graph comparing the coefficient of friction of microspheres of melamine formaldehyde polymer with other materials.

FIG. 2 presents a graph comparing the coefficient of friction for microspheres of polymerized melamine formaldehyde resin according to the invention (MP in FIG. 2) with the coefficients for spherical silica, titanium dioxide, talc, porous spherical nylon, and boron nitride. The comparison uses the ASTM D1884-95 test method. The coefficient of friction is the measure of drag between two surfaces moving in different directions.

The graph reveals a coefficient of friction of approximately 0.1 for microspheres of polymerized melamine formaldehyde resin, 0.4 for talc, 0.41 for boron nitride, 0.6 for spherical silica, 0.61 for porous spherical nylon, and 0.7 for titanium dioxide.

Low coefficient of friction values correspond to the degree of smoothness provided by a component in a formulation. Accordingly, microspheres of polymerized melamine formaldehyde resin according to the invention as a component in a cosmetic formulation provide a high degree of smoothness to the formulation producing a silky feel.

Microspheres of melamine formaldehyde are formed by a process identified as emulsion-polymerization. In this process three steps are involved.

First, melamine and formaldehyde are reacted under conditions of extreme heat 260° C. and pressure 85 psig resulting in a very water-intolerable resin. The resin is very sticky and adhesive in nature.

Second, the resin is emulsified in water resulting in very fine droplets of resin. These droplets are polymerized to obtain very fine solid round particles.

Third, the processing water is removed leaving very fine solid particles having the size and coefficient of friction described above.

Various changes may be made to the structure embodying the principles of the invention. The foregoing embodiments are set forth in an illustrative and not in a limiting sense. The scope of the invention is defined by the claims appended hereto.

I claim:

1. Microspheres of polymerized melamine formaldehyde resin in spherical form with the microspheres having particle size in a range of 5–15 microns.

2. Microspheres of polymerized melamine formaldehyde resin in spherical form with the microspheres having particle size in a range of 5–15 microns and a coefficient of friction lower than the coefficient for talc.

3. Microspheres of polymerized melamine formaldehyde resin in spherical form with the microspheres having a coefficient of friction approximately one-quarter of the coefficient of friction for talc.

4. Microspheres of polymerized melamine formaldehyde resin in spherical form with the microspheres having a coefficient of friction of approximately 0.1 using the ASTM D1884-95 test method.

5. Microspheres of polymerized melamine formaldehyde resin as defined in claim 4 in which the microspheres have a particle size in a range of 5–15 microns.

6. A cosmetic formulation containing microspheres of polymerized melamine formaldehyde resin in spherical form with the microspheres having particle size in a range of 5–15 microns for imparting smoothness to the formulation.

7. A cosmetic formulation containing microspheres of polymerized melamine formaldehyde resin in spherical form with the microspheres having particle size in a range of 5–15 microns for imparting opacity to the formulation.

8. Microspheres of polymerized melamine formaldehyde resin which are perfectly spherical in form with the microspheres having particle size in a range of 5–15 microns, and a coefficient of friction less than talc.

* * * * *